United States Patent [19]
Ellis et al.

[11] Patent Number: 4,963,483
[45] Date of Patent: Oct. 16, 1990

[54] METHOD FOR PRODUCING HEPATITIS B VIRUS PROTEINS IN YEAST

[75] Inventors: Ronald W. Ellis, Overbrook Hills; Arpi Hagopian; Peter J. Kniskern, both of Lansdale; Donna L. Montgomery, Chalfont, all of Pa.

[73] Assignee: Merck & Co., Inc., Rahway, N.J.

[21] Appl. No.: 107,812

[22] Filed: Oct. 13, 1987

[51] Int. Cl.$^5$ .................. C12N 15/00; C12N 5/00; C12P 21/00; A61K 39/00
[52] U.S. Cl. .................. 435/69.3; 435/69.1; 435/71.1; 435/172.3; 435/255; 435/256; 435/320; 935/28; 935/37; 935/69
[58] Field of Search .............. 435/68, 255, 69.3, 69.1, 435/172.3, 71.1, 256, 320; 935/69, 28, 37

[56] References Cited
U.S. PATENT DOCUMENTS
4,477,571 10/1984 Chang et al. .................... 435/252.33

OTHER PUBLICATIONS
Bitter, et al. Gene 32:263-274, 1984.
Holland, et al. J. Biol. Chem 255:2596-2605, 1980.
Itoh, Y. Biochim, Biophip Res Comm 138(1): 268-274, 1986.
Valenzuela et al., EP Patent Application 0 174 444.
Budkowska, et al.; Ann. Inst. Past./Immuno. 136D:57-65 (1986).
Petit et al., Mol. Immun. 23:511-523 (1986).
Milich et al., PNAS 82:8168-8172 (1985).
Neurath et al., J. Med. Virol 17:119-125 (1985).
Neurath et al., Vaccine 4:34-37 (1986).
Itoh et al., PNAS USA 83:9174-9178 (1986).
Hilleman et al., Vaccine 4:75-76 (1986).
Scolnick et al., JAMA 251:2812-2815 (1984).
Valenzuela et al., Botechnology 3:317-320 and 292 (1985).

Primary Examiner—Robin L. Teskin
Assistant Examiner—Beth A. Burrous
Attorney, Agent, or Firm—Donald J. Perrella; Hesna J. Pfeiffer

[57] ABSTRACT

The hepatitis B virus preS2 antigen gene linked in one contiguous reading frame to the hepatitis B virus surface antigen gene has been expressed in Saccharomyces cerevisiae utilizing an optimized plasmid construction. The expressed protein aggregates into a particulate form which displays the major antigenic sites encoded by both domains, thereby highlighting the utility of yeast as a host for the high level expression of the preS2 as well as the S domain. This protein is useful in in vitro diagnostic systems and as a vaccine for the treatment and prevention of hepatitis B virus-induced diseases and/or infections.

13 Claims, 1 Drawing Sheet

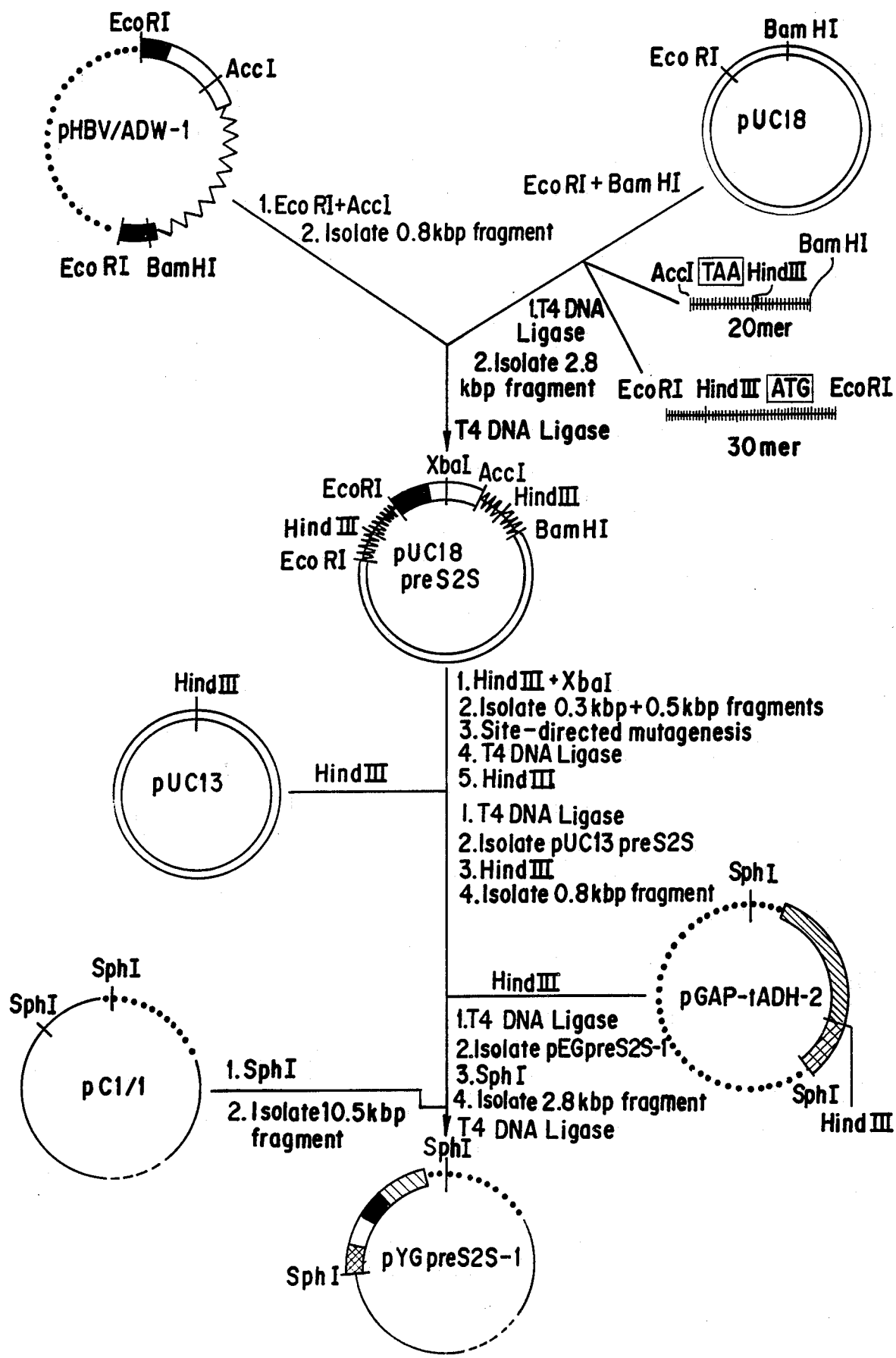

METHOD FOR PRODUCING HEPATITIS B VIRUS PROTEINS IN YEAST

BACKGROUND OF THE INVENTION

Hepatitis B virus (HBV) is the infectious agent responsible for several varieties of human liver disease. Many individuals who are infected by HBV suffer through an acute phase of disease, which is followed by recovery. However, a large number of individuals fail to clear their infection, thereby becoming chronic carriers of the infection. HBV infection is endemic to many parts of the world, with a high incidence of infection occurring perinatally from chronically infected mothers to their newborns. The number of chronic carriers worldwide has been estimated at over three hundred million. From this pool of carriers, hundreds of thousands die annually from the long term consequences of chronic hepatitis B (cirrhosis or hepatocellular carcinoma).

The HB virion is composed of two groups of structural proteins, the core proteins and the envelope or surface ("S") proteins. In addition to being the major surface proteins of the virion, i.e., Dane particle, the "S" proteins are the sole constituents of Australia antigen, or 22 nm particles. The "S" proteins are the translational products of a large open reading frame (ORF) encoding 389 amino acids. This ORF is demarcated into three domains, each of which begins with an ATG codon that is capable of functioning as a translational initiation site in vivo. These domains are referred to as preS1 (108 amino acids), preS2 (55 amino acids), and S (226 amino acids) in their respective 5'-3' order in the gene. Thus, these domains define three polypeptides referred to as S or HBsAg [226 amino acids (aa)], preS2+S (281 aa), and preS1+preS2+S (389 aa). Currently available plasma-derived vaccines are composed of proteins containing virtually only the S domain, while yeast derived vaccines successfully developed to date are composed exclusively of the S polypeptide.

The 22 nm particles, or HB surface antigen (HBsAg) particles, have been purified from the plasma of chronic carriers. In terms of their plasma being particle-positive, these chronic carriers are referred to as HBs+. When these carriers have mounted a sufficient immune response, they can clear the infection and become HBs−. In terms of their formation of antibodies to HBs, these individuals are denoted anti-HBs+. In this way, anti-HBs+ is correlated with recovery from disease. Therefore, the stimulation or formation of anti-HBs+ by HB vaccines has been expected to confer protection against HBV infection.

This hypothesis has been testable experimentally. Outside of man, chimpanzees are the only species which is fully susceptible to HBV infection, as reflected in quantifiable markers such as HBs+, and elevated serum levels of liver enzymes. Chimpanzees have been vaccinated with three doses of purified HBsAg particles and then challenged with a large dose of infectious HBV. While mock-vaccinated animals have suffered the signs of acute HBV infection, the HBsAg-vaccinated animals have been protected completely from any signs of infection. Therefore, in this experimental system, HBsAg particles, composed of gp27 and p24 (S domain only), have been sufficient to induce protective immunity. Spurred by these observations, several manufacturers have produced HB vaccines composed of HBsAg particles.

Recently, several independent lines of evidence have suggested the preS sequences may be important in immunity to HBV. The immune elimination of preS antigens during the course of viral infection appears prognostic for viral clearance and abrogation of infection [Budkowska et al., Ann. Inst. Past./Immun. 136D:56–65, (1985)]. During acute hepatitis B, antibodies to preS often arise earlier than antibodies to S [Petit et al., Mol. Immun. 23:511–523, (1986)]. In inbred mice, the immune responses to S and preS appear to be regulated independently, and the presence of preS influences the immune response to S [Milich et al., Proc. Nat. Acad. Sci. USA 82:8168–8172, (1985), J. Immunol. 137:315–322 (1986); Neurath et al., J. Med. Virol. 17:119–125, (1985)]. Furthermore, antibodies to preS neutralize viral infectivity in vitro [(Neurath et al., Vaccine, 4:35–37, 1986)]and preS antigens protect immunized chimpanzees [Itoh et al., Proc. Nat. Acad. Sci. USA 83:9174–9178, (1986)]. In light of these observations and because of the utility of recombinant yeast in producing HB vaccines [Hilleman et al., Vaccine 4:75–76, (1986)], we have formulated experimental preS-containing HB vaccines from recombinant *S. cerevisiae*.

In order to expand the available supply of HB vaccines, manufacturers have turned to recombinant DNA technology to mediate the expression of "S" proteins. Among microbial systems, *Escherichia coli* and *Saccharomyces cerevisiae* have been used most commonly for the expression of many recombinant-derived proteins. Numerous attempts to express immunologically active HBsAg particles in *E. coli* have been unsuccessful. However, *S. cerevisiae* has shown great versatility in its ability to express immunologically active HBsAg particles. These particles, when formulated into a vaccine, have proven capable of fully protecting chimpanzees against challenge with live HBV. Furthermore, yeast derived HBsAg has shown the ability to express immuno-logically logically active HBsAg particles which have been as effective in human clinical trials as plasma derived HBsAg [Scolnick et al., JAMA 251: 2812–2815 (1984)]. Therefore, the utility of *S. cerevisiae* as a host species for directing synthesis of recombinant HBsAg is established firmly. In addition, expression of human therapeutic agents and vaccines in yeast can be very useful for product development, since yeast is free of endotoxin, is nonpathogenic to man, can be fermented to industrial scale, and lacks many of the safety concerns which surround the use of continuous mammalian cell lines (many of which are virally transformed, may be tumorigenic in mice and all of which contain protooncogenes).

OBJECTS OF THE INVENTION

Therefore, it is an object of the present invention to provide expression vectors and processes for the optimized high yield expression of preS2+S in yeast as an immunogenic particle. Another object of this invention is to specify conditions for the scale-up of the growth of recombinant host cells transformed by such optimized vectors, such that maximal yields of preS2+S may be attained in much larger volumes and in higher concentrations for the purification of such polypeptides. These and other objects of the present invention will be apparent from the following description.

BRIEF DESCRIPTION OF THE DRAWINGS

FIG. 1 shows diagramatically the preparation procedure of pYGpreS2S-1, the preS2+S expression plasmid.

SUMMARY OF THE INVENTION

The preS2+S gene has been expressed at an optimized high yield in yeast. The expressed protein aggregates into a particulate form which displays the major antigenic sites encoded by plasma derived preS2+S, thereby highlighting the utility of yeast as a host for the expression of this gene. This protein is useful for in vitro diagnostic systems and as a vaccine for the prevention of HBV-induced infections.

DETAILED DESCRIPTION OF THE INVENTION

The present invention is directed to a method for the expression of preS2+S in yeast species.

Dane particles are utilized as the source of HBV nucleic acid (for the isolation of the open reading frame (ORF) of preS2+S. The endogenous polymerase reaction is employed in order to produce covalently-closed circular double stranded DNA of the HBV genome from the nicked and gapped nucleic acid form that natively resides in the HB virion. The DNA is isolated, digested to completion with the restriction enzyme EcoRI, and cloned into the EcoRI site of plasmid pBR322 generating plasmid pHBV/ADW-1. The recombinant plasmids thus produced are selected, those containing the HBV genome in a circularly permuted form at the EcoRI site of the PreS region. The complete ORF encoding the 55 amino acids of the preS2 region and the 226 amino acids of the S region was constructed by first purifying the 0.8 kilobase pair (kbp) fragment obtained following digestion of pHBV/ADW-1 with EcoRI and AccI; this fragment encodes the preS2+S polypeptide lacking only the initiation codon, the amino terminal 3 amino acids, the carboxy-terminal 3 amino acids, and the translational terminator codon. Oligonucleotides were synthesized and ligated to this fragment, converting it to a HindIII fragment containing a 10 bp yeast derived non translated 5' flanking sequence and the complete preS2+S ORF. A high-yield, expression system for the production of the foreign gene HBV preS2+2 is a primary object of this invention. It is through the genetically tailored interaction of the expression-vector (specifically the promoter and transcriptional terminator) with the inserted ORF that the highest levels of a foreign gene product can be obtained in the yeast host cell. This ratio of the concentration of the expressed foreign protein product to total yeast cell proteins is referred to as "specific activity". A high initial specific activity allows for rapid and economical isolation of the product with a high degree of purity, efficacy and, concomitantly, safety as a human vaccine.

The following reasoning was employed in the construction of this yeast expression vector [comprised of the GAP491 (glyceraldehyde phosphate dehydrogenase) promoter and the ADH1 (alcohol dehydrogenase) transcriptional terminator]with the inserted foreign gene ORF (HBV preS2+2). It was reasoned that optimization has occurred evolutionarily in the yeast genes encoding highly expressed natural yeast proteins. Therefore, a consensus sequence or specific sequence derived from the 5' and 3' flanking regions of such genes should also be optimal for foreign gene expression by enhancing transcription rate, message stability, and translation rate.

The sequence at the 3' flank of the PreS2+S ORF was chosen such that the termination codon directly abutted a natural HindIII site in the ADH1 transcriptional terminator, thus creating a completely native yeast-derived junction without any additional intervening bases. It is obvious to those skilled in the art that for optimized high-level expression of preS2+S (or other foreign gene), any suitable yeast transcriptional terminator may be substituted for ADH1.

The 5' flanking sequence for the optimized construct (ACAAAACAAAA) was chosen to correspond to that for the non translated leader (NTL) of a highly expressed glyceraldehyde-3-phosphate dehydrogenase gene [GAP63) Holland, J. Biol. Chem., 225, 2596 (1980)]and is also a consensus for the GAP gene family. The construction was made in such a manner as to abut the NTL directly to the initiation codon of the preS2+S ORF without intervention of any additional bases. It is obvious, therefore, to those skilled in the art that for optimized high-level expression of preS2+S, the selection of non translated leader sequences extends to other highly expressed yeast genes including but not limited to GAP491, GAP11, Enolase, ADH1, ADH2, PHO5, and the like.

DNA sequence analysis revealed 2 base substitutions which resulted in amino acid differences from the preS2+S sequence encoded by the DNA of plasmid pHBpreSGAP347/19T (described in European patent application No. 0 174 444 as pHBpreS56GAP347/33). In order to evaluate identical polypeptides for both constructions, these substitutions, which were T instead of C at base 64 (encoding Phe rather than Leu) and C instead of A at base 352 (encoding His rather than Gln) were changed by site-directed mutagenesis [Zoller et al., Nucleic Acids Research 10:6487–6500 (1982)]. The encoded amino acid sequence for the optimized construction then was verified.

Following mutagenesis, the fragment described above was used to construct an expression cassette, as described previously [Kniskern et al., Gene 46:135–141, (1986)], which was composed of: (a) ca. 1050 bp of the GAP491 promoter, (b) a 10 bp yeast derived flanking sequence, (c) 846 base pairs of the HBV preS2+S gene (serotype adw) lacking any viral flanking sequences, and (d) ca. 350 bp of the yeast ADH1 terminator. This expression cassette was inserted into the yeast shuttle vector pCl/1 [Beggs, Nature 275:104 (1978); Rosenberg et al., Nature 312:77, (1984)]and used to transform yeast strain CF42 (generating transformant pYGpreS2S-1). In a parallel experiment, the plasmid pHBpreSGAP347/19T was used to prepare a fresh transformant of the same parental yeast strain CF42 (generating transformant pGpreS2S-2). These transformants were established as frozen stocks for evaluation and subsequent experimentation. Parental strain CF42 was obtained as follows: a spontaneous ura3 mutation in yeast strain 2150-2-3 (gift of L. Hartwell, U. of Washington) was selected (Boeke et al., Mol. Gen. Genet. 197:345 346, 1984). The resulting strain (MATa, adel, leu2-04, ura3, cir°) was diploidized by transforming with plasmid YCp50 HO [Jensen et al., P.N.A.S. USA 80:3035–3039(1983)]. The functional yeast gene HO allows cells to switch mating type. Thus, progeny from single cell transformants will be a mixture of both "a" and "α" mating types and will mate during colony growth. A diploid clonal isolate was cured of the plasmid and designated CF42, (MATa/α, adel, leu2-04, ura3). These transformants were established as frozen stocks for evaluation and subsequent experimentation.

Recombinant yeast from the above frozen stocks are grown in YEHD medium. After growth to stationary phase, yeast cells are harvested, and lysates are prepared, resolved by sodium dodecylsulfate polyacrylamide electrophoresis (SDS-PAGE) and immunoblotted with antibodies to HBsAg. Two major polypeptides are found with molecular weights of 30- and 34-kilodaltons (kD) in accord with the predicted molecular weight of the translational product of the preS2+S ORF and its glycosylated derivative. Furthermore, lysates of recombinant, but not parental yeast, are positive for preS2+S by radioimmunoassay. Electron microscopic examination of partially purified yeast lysates shows high densities of typical 22nm preS2+S particles.

The yeast-derived promoter initiates transcription of the preS2+S gene. Therefore, it is obvious to those skilled in the art that any yeast promoter may be substituted for the GAP491 promoter. It is also obvious to those skilled in the art that a suitable assay system, e.g., immunoblot or radio-immunoassay or enzyme-linked immunoassay (EIA), should be utilized in order to assay expression of preS2+S polypeptides in this system, such that the time of harvesting of the culture for attaining a maximal yield can be optimized.

The GAP491 promoter has been useful for the expression in yeast of several foreign proteins, including HBsAg [Bitter et al., Gene 32:263-274, (1984), Wampler et al, Proc. Nat. Acad. Sci. USA 82:6830-6834 (1985)]. Based upon our previous results of expressing HBcAg to ca. 40% of soluble yeast protein (Kniskern et al., supra) we sought to optimize the expression of preS2+S antigen from this promoter. The two expression plasmids for preS2+S, pYGpreS2S-1 and pHBpreSGAP347/19T, encode polypeptides of identical amino acid sequence. They differ in their non-translated flanking sequences, in that the former contains an optimized 5' sequence, no viral 5' or 3' sequences, and yeast ADH1 transcriptional terminator, while the latter contains ca. 130 bp of HBV derived 3' flanking sequences and the GAP491 transcriptional terminator. Both vectors were used to transform yeast strain CF42, the transformants of which then were assayed in parallel shake flask experiments. The amounts of preS2+S in yeast transformed by pYGpreS2 1 were reproducibly 4 to 5-fold higher than for transformants by pHBpreSGAP347/19T.

The DNA sequence flanking the initiation signal [i.e., the 5' non-translated leader (NTL)]is thought to have an important effect on gene expression levels by influencing transcription rate, message stability, and translation rate. Evolution through natural selection probably has optimized the 5' NTL sequences for native yeast genes (e.g. the glycocidic enzymes) for which the high-level expression would present a survival advantage. For the construction described herein, the concensus 5' NTL sequence, ACAAAACAAAA, which is derived from the 5' NTL sequence of the GAP gene family, has been used to enhance and optimize the expression level of the HBV PreS2+S ORF and it will be obvious to those skilled in the art that any 5' NTL with concensus derived from the 5' NTL of highly expressed native yeast genes will also be useful.

The genus *Saccharomyces* is composed of a variety of species. The most commonly used is *Saccharomyces cerevisiae*, or baker's yeast, as a host for the recombinant DNA-mediated expression of a variety of foreign polypeptides. However, the distinctions among other species of the genus *Saccharomyces* are not always well defined. Many of these species are capable of interbreeding with *S. cerevisiae* and are likely to possess promoters which are analogous to or identical to promoters in *S. cerevisiae*. Therefore, it will be obvious to those skilled in the art that, for the expression of preS2+S polypeptides, the selection of a host strain extends to other species of the genus *Saccharomyces*, including but not limited to carlsbergensis, uvarum, rouxii, montanus, kluyveri, elongisporus, norbensis, oviformis, and diastaticus.

Several yeast genera, such as Hansenula, Candida, Torulopsis, and Pichia, have been shown to contain similar metabolic pathways for the utilization of methanol as a sole carbon source for growth. The gene for alcohol oxidase, an enzyme which participates in this metabolic pathway, has been isolated from *Pichia pastoris*. The *P. pastoris* alcohol oxidase promoter has been isolated and shown to be susceptible to methanol induction of expression. Such an inducible promoter is useful for the expression of polypeptides in yeast. In particular, this promoter has been shown to be active on a plasmid for the inducible expression of the HBV "S" domain in *P. pastoris* in particulate form. This observation highlights the ability of other yeast genera to function as hosts for the recombinant DNA-mediated expression of polypeptides in immuno-logically active form. Therefore, it will be obvious to those skilled in the art that, for the expression of preS2+S, the selection of a host strain extends to species from other genera of yeast from the Families Saccharomycetaceae and Cryptococcaceae, including, but not limited to Pichia, Candida, Hansenula, Torulopsis, Kluyveromyces, and Saccharomycopsis.

The following examples illustrate the present invention without, however, limiting the same thereto. The disclosure of each reference mentioned in the following examples is hereby incorporated by reference.

EXAMPLE 1

Cloning of HBV DNA in pBR322

HBV Dane particles (serotype adw) were isolated and purified from human plasma (carrier), and double-stranded DNA was synthesized by endogenous polymerase in the Dane particles according to the methods of Landers et al, [J. Virology 23, 368–376 (1977)]and Hruska et al, [J. Virology 21, (1977)]. The DNA was isolated after digestion with Proteinase K in SDS followed by extraction with phenol/chloroform and ethanol precipitation. The HBV genomic DNA was digested with EcoRI, producing a single 3.2 kbp fragment, and cloned into the EcoRI site of pBR322. The presence of the HBV DNA was confirmed by EcoRI digestion, Southern blot transfer to nitrocellulose, and hybridization with [$^{32}$P]-labelled specific oligonucleotide probes. This plasmid is referred to as pHBV/ADW-1 (FIG. 1).

EXAMPLE II

Cloning of the preS2+S Gene into the pGAP-tADH 2 Expression Vector

As shown in FIG. 1, plasmid pHBV/ADW-1 (described in Example I) was digested with EcoRI and AccI and the 0.8 kbp fragment purified by preparative agarose gel electrophoresis.

To reconstruct the 5' portion of the preS2+S ORF, a pair of oligonucleotides was synthesized which reconstitutes the ORF from the EcoRI site upstream to the ATG through a 10bp NTL sequence to a HindIII terminus. The sequence of this oligonucleotide is:

AGCTTACAAAACAAAATGCAGTGG
ATGTTTTGTTTTACGTCACCTTAA

To reconstitute the 3' portion of the preS2+S ORF, a second pair of oligonucleotides was synthesized which reconstitutes the ORF from the AccI site through the translational terminator to a HindIII terminus. The sequence of this oligonucleotide is:

ATACATTTAATGTAAATTTCGA

The plasmid pGAP tADH 2 (see FIG. 1) containing the GAP491 promoter [Holland et al., J. Biol. Chem. 255:2596 (1980)]and the ADH1 transcriptional terminator in pBR322, has a unique HindIII cloning site into which the preS2+S ORF described above was ligated, yielding pEGC 1 (FIG. 1). The presence and orientation of HBsAg DNA was confirmed by restriction endonuclease analyses and Southern blot transfer. The expression cassette containing the preS2+S ORF was removed from pEGpreS2S-1 by SphI digestion and isolated by preparative agarose gel electrophoresis. The cassette was then cloned into the shuttle vector pC1/1 [Beggs, supra; Rosenberg et al., supra] which had been digested previously with SphI. The resultant plasmid containing the expression cassette was used to transform S. cerevisiae strain CF42, (MATa/α, adel leu2-04, ura3), which was created as follows:

A ura3 mutation in yeast strain 2150-2-3 (gift of L. Hartwell, U. of Washington) was selected (Boeke et al., supra). The resulting strain (MATa, adel, leu2 04, ura3, cir°) was diploidized by transforming with the plasmid YCp50·HO. A diploid strain was cured of the plasmid and designated CF42, (MATa/α, adel, leu2-04, ura3).

Clones were selected and established as frozen stocks (in 17% glycerol) for evaluation as described in example III.

EXAMPLE III

Growth and Expression of the preS2+S Gene

Clones of yeast containing the expression plasmid described in Example II were suspended in 0.2-0.3 ml H2O, plated onto leucine⁻ selective agar plates, and incubated at 30° for 2-3 days. These yeast were inoculated into 5-7 ml cultures of complex YEHD media and the cultures were incubated at 30° with aeration for 12-18 hours. Flasks containing 50 ml complex YEHD media were inoculated from the above cultures at a dilution 1:25 and were incubated at 30° C. with shaking (350 rpm) for 48-72 hours to a final $A^{600}$ of 10.0-16.0. Duplicate samples of 10 $A^{600}$ units were aliquoted into tubes, and the yeast cells were pelleted at 2000×g for 10 min. The pellets were resuspended in 0.4 ml of phosphate buffered saline containing 2 mM phenylmethyl sulfonyl fluoride and transferred to 1.5 ml eppendorf tubes. Yeast cells were broken by the addition of 200-300 mg of washed glass beads (0.45mm) and agitation on a vortex mixer for 5-15 min. Cellular debris and glass beads were removed by centrifugation at 2000×g for 10 min. The clarified supernatant fluid was removed and assayed for protein [by the method of Lowry et al., J. Biol. Chem. 193, 265 (1951)]and radioimmuno-assay specific for preS2+S [Hansson et al., Infect. Immunol. 26: 125-130 (1979), Machida et al., Gastroenterology 86: 910-918 (1984)]. Levels of expression were estimated to be 4-5 fold higher than that obtained from the parental yeast transformed with plasmid pHBpreS-GAP347/19T (Table 1).

TABLE 1

Expression of preS2 + S in yeast utilizing different expression plasmids

| Plasmid | Relative productivity[a] in yeast strain | |
|---|---|---|
| | 2150-2-3 | CF42 |
| pHBpreSGAP347/19T | 1.0[b] | 1.2 |
| pYGpreS2S-1 | ND[c] | 5.6 |

[a]Clarified yeast cell extracts (Kniskern et al., supra) were assayed for preS2 + S antigen by radioimmunoassay and for protein content. Each clone was cultured, lysed and assayed in duplicate, such that relative values represent the mean of 8 determinations of volumetric productivity.
[b]The productivity levels in μg antigen/mg protein are standardized relative to a value of 1.0 for this transformant.
[c]ND = not done

EXAMPLE IV

Large Scale Growth and Purification of PreS2+S

Yeast cells were grown as described (Wampler et al., supra) and harvested by filtration using an Amicon DC30 with hollow fiber membranes. Harvested cells were frozen at −70° until use. Frozen cells expressing preS2+S polypeptides were thawed and resuspended in 0.1M HEPES buffer, pH 7.5 containing 10 mM ethylenediaminetetraacetic acid, 10 mM benzamidine-HCl, 1 mcg/mL pepstatin A and 0.13 trypsin inhibitor units/mL aprotinin. Immediately before breaking, phenylmethylsulfonylfluoride (200 mM in 2 propanol) was added to a final concentration of 2 mM and the cells were disrupted with three passes through a Stansted press (Energy Services Corp., Washington, D.C.), yielding a yeast cell lysate. Cell debris was removed by two phase extraction between PEG 3350 and Dextran T500. The upper PEG phase containing the preS2+S antigen was recovered, and the antigen was isolated by immune-affinity chromatography as previously described [Wampler et al., In Chanock and Lerner (eds.): "Modern Approaches to Vaccines," Cold Spring Harbor, NY, Cold Spring Harbor Press, pp. 251-256 (1984)]. Residual goat IgG was removed by passing the concentrated antigen through a 2.6×28 cm column of Sephacryl S400 which had been equilibrated with 0.1 M phosphate buffer, pH 7.2 containing 3M NH4SCN and 0.5M NaCl. NH4SCN was removed by diafiltration against phosphate-buffered saline. Purified preS2+S antigens were adsorbed to aluminum hydroxide for in vivo testing.

What is claimed is:

1. A plasmid expression vector containing yeast-derived sequences for the selection and amplification of the plasmid in a species of yeast derived from the families *Saccharomycetaceae* or *Cryptococcaceae*, a yeast promoter, a nontranslated leader having the nucleotide sequence ACAAAACAAA, the preS2+ S hepatitis B virus coding region, and a yeast transcriptional termination sequence, the 3' end of the yeast promoter abutting the end of 5' nontranslated leader and the 3' end of nontranslated leader abutting the initiation codon of the preS2+S coding region.

2. A plasmid according to claim 1 wherein the termination codon of the preS2+S coding region abuts the yeast transcriptional termination sequence.

3. A plasmid according to claim 1 wherein 5' nontranslated leader is selected from a highly expressed or overexpressed native yeast gene.

4. A plasmid according to claim 3 wherein the highly expressed or overexpressed native yeast gene is the glyceraldehyde phosphate dehydrogenase gene.

5. A species of yeast derived from the families *Saccharomycetaceae* or *Crytococcaceae* containing a plasmid of claim 1.

6. A species of yeast according to claim 5 wherein the species is from the genus *Saccharomyces*.

7. A species of yeast according to claim 6 wherein the species in *Saccharomyces cerevisiae*.

8. A composition of a species of yeast from the families *Saccharomycetaceae* or *Cryptococcaceae* which has been transformed with a plasmid expression vector of claim 1.

9. A composition according to claim 8 wherein the species is from the genus *Saccharomyces*.

10. A composition according to claim 9 wherein the species is *Saccharomyces cerevisiae*.

11. A process for obtaining the preS2+S polypeptide comprising:
   a. transforming cells from a strain selected from the families *Saccharomycetaceae* or *Cryptococcaceae* with a plasmid expression vector of claim 1,
   b. culturing the transformed cells, and
   c. recovering the peptide from the resulting cultured cells or growth medium.

12. A process according to claim 11 wherein the species is from the genus *Saccharomyces*.

13. A process according to claim 12 wherein the species is *S. cerevisiae*.

* * * * *